(12) United States Patent
Lee (10) Patent No.: US 11,504,301 B2
(45) Date of Patent: Nov. 22, 2022

(54) BALLOON TYPE LIQUID MEDICINE INJECTOR

(71) Applicant: Jeehee Lee, Seoul (KR)

(72) Inventor: Jeehee Lee, Seoul (KR)

(*) Notice: Subject to any disclaimer, the term of this patent is extended or adjusted under 35 U.S.C. 154(b) by 154 days.

(21) Appl. No.: 17/000,947

(22) Filed: Aug. 24, 2020

(65) Prior Publication Data

US 2021/0052466 A1 Feb. 25, 2021

(30) Foreign Application Priority Data

Aug. 22, 2019 (KR) .................. 10-2019-0103094

(51) Int. Cl.
| | | |
|---|---|---|
| *A61M 5/152* | (2006.01) | |
| *A61J 1/14* | (2006.01) | |
| *A61J 1/20* | (2006.01) | |
| *A61M 5/148* | (2006.01) | |

(52) U.S. Cl.
CPC .......... *A61J 1/1475* (2013.01); *A61J 1/2048* (2015.05); *A61M 5/148* (2013.01); *A61M 5/152* (2013.01)

(58) Field of Classification Search
CPC ........ A61M 5/142; A61M 5/14; A61M 5/168; A61M 5/152; A61M 5/148; A61J 1/1475; A61J 1/2048
See application file for complete search history.

(56) References Cited

U.S. PATENT DOCUMENTS

| | | | | | |
|---|---|---|---|---|---|
| 3,677,444 | A | * | 7/1972 | Merrill | F04F 3/00 604/407 |
| 4,227,293 | A | * | 10/1980 | Taylor | B23P 11/025 29/447 |
| 4,915,693 | A | * | 4/1990 | Hessel | A61M 5/152 604/132 |
| 5,080,652 | A | * | 1/1992 | Sancoff | A61M 5/152 222/105 |
| 5,211,632 | A | * | 5/1993 | Tsukada | A61M 5/152 604/246 |
| 5,529,214 | A | * | 6/1996 | Lasonde | B65D 83/0061 222/105 |

FOREIGN PATENT DOCUMENTS

| | | |
|---|---|---|
| KR | 10-1125478 B1 | 3/2012 |
| KR | 10-1535947 B1 | 7/2015 |
| KR | 10-2049701 B1 | 1/2020 |

* cited by examiner

*Primary Examiner* — Ariana Zimbouski
(74) *Attorney, Agent, or Firm* — Jefferson IP Law, LLP (57) ABSTRACT

A balloon type liquid medicine injector for continuously injecting a small amount of liquid medicine into a body of a patient is disclosed as to be easily assembled and to prevent unnecessary dead space while being inflated after a liquid medicine is injected, so as to be miniaturized. When a tube body is provided outside a fixed pipe, both ends of the tube body are folded and inserted into both ends of the fixed tube, to remove the dead space while being inserted inside the case. In addition, in a state where the both ends of the tube body are folded and inserted into the both ends of the fixed tube, an injection mechanism for injecting the liquid medicine or a stopper mechanism are coupled while pressing the tube body folded inward, so that a separate packing is unnecessary and the airtightness is maintained.

13 Claims, 14 Drawing Sheets

BALLOON TYPE LIQUID MEDICINE INJECTOR

CROSS-REFERENCE TO RELATED APPLICATION(S)

This application is based on and claims priority under 35 U.S.C. § 119(a) of a Korean patent application number 10-2019-0103094, filed on Aug. 22, 2019, in the Korean Intellectual Property Office, the disclosure of which is incorporated by reference herein in its entirety.

BACKGROUND OF THE INVENTION

1. Field of the Invention

The present disclosure relates to a balloon type liquid medicine injector for continuously inject a small amount of liquid medicine into a body of a patient, and more particularly, to a balloon type liquid medicine injector that is easily assembled and prevents an unnecessary dead space while being inflated after a liquid medicine is injected, so as to be miniaturized.

2. Description of the Related Art

In general, liquid medicines such as antibiotics or painkillers are required to be continuously administered patients, who have undergone urgent surgery for cancer or leukemia or the like, to relieve pain as well as remove inflammation after the surgery.

Though there is a difference between patients, another urgent situation may occur to the patient when the liquid medicine is administered to the patient at an amount more than or less than an optimum amount.

Thus, separate injection devices are used to continuously inject a fine amount in order to solve the above problem. However, the above injection devices are quite expensive, occupy a lot of spaces, and are inconvenient when being carried, and accordingly the injection devices cannot be provided individually to a lot of patients.

Accordingly, recently, balloon-type liquid medicine injectors, which are usable as a personal type, portable and inexpensive and facilitate a continuous injection, are used.

Figure 1:
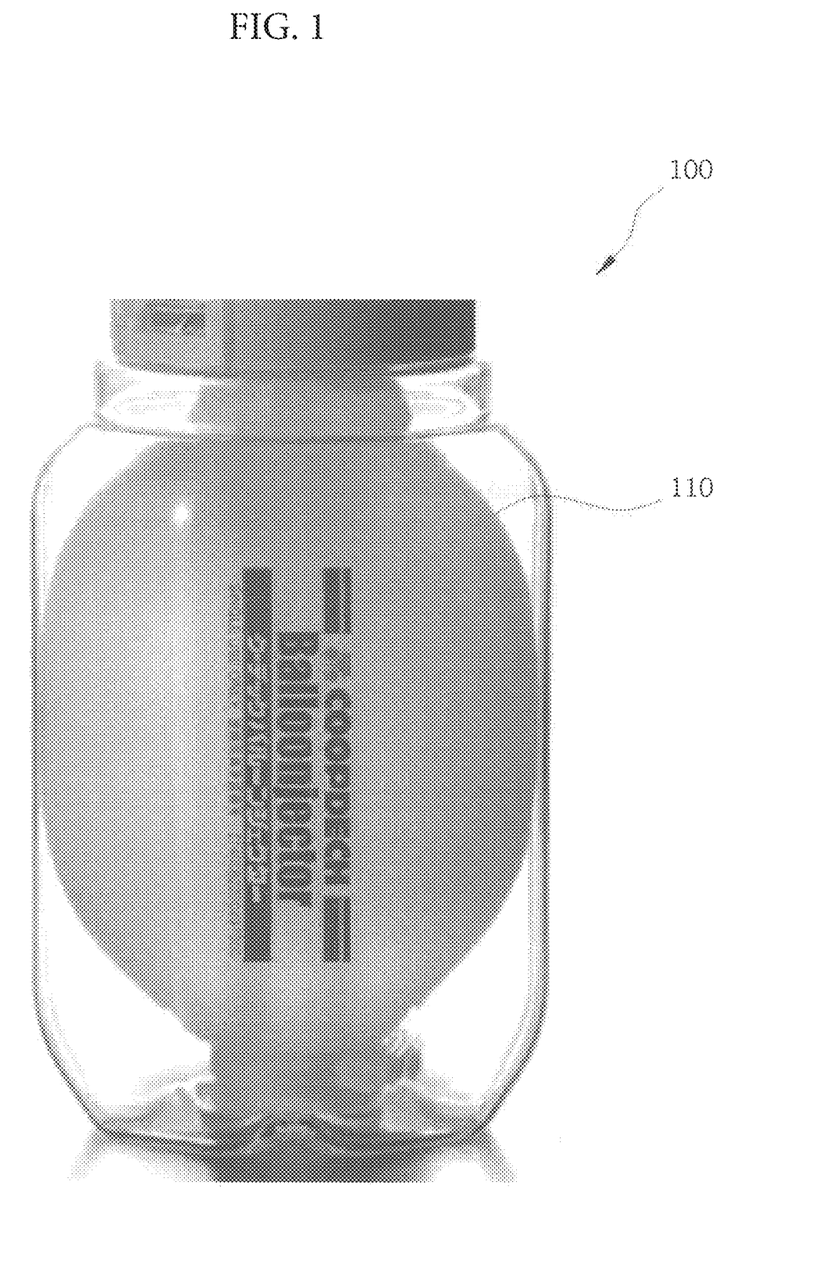
FIG. 1 is a view showing an appearance state of a conventional balloon-type liquid medicine injector.

A balloon type liquid medicine injector 100 currently used includes a tube body 110 inflated when filled with a liquid medicine to discharge the injected liquid medicine while returning to an initial position from the inflated state, as shown in FIG. 1. For the above-described operation of the tube body, a fixed tube having a flow path for the liquid medicine at a predetermined position therein is installed inside the tube body. In order to fix the tube body when the tube body surrounding the fixed tube is contracted and inflated, upper and lower ends of the fixed tube is fixed using a fixing mechanism from the outside of the tube body surrounding the fixed tube, so that the tube body is fixed while maintaining the airtightness between the fixed tube and the tube body.

Accordingly, when the upper and lower ends of the fixed tube are fixed using the fixing mechanism, the fixed tube or the fixing mechanism is used for the firm fixation by the fixing mechanism in a special scheme.

For example, in order to prevent the fixing mechanism from slipping when the tube body is inflated while being fixed by the fixing mechanism, a locking groove, for example, may be formed on an outer wall of the fixed tube, a slip prevention mechanism may be provided at the fixing mechanism slipping, or the fixing mechanism may be spaced apart from the upper and lower ends of the fixed tube at a predetermined distance.

According to the above using scheme, since the fixing mechanism is positioned and fixed at the portions spaced apart from the upper and lower ends of the fixed tube at the predetermined distance, a dead space eventually exists in the above portions in a state where a case used for protecting the tube body is combined.

In addition, the liquid medicine is injected into the fixed tube while the tube body is fixed by the fixing mechanism. In the above case, an injection mechanism for injecting the liquid medicine is mounted at one end of the fixed tube. In addition, the other end is provided with a stopper mechanism for maintaining the airtightness to allow the injected liquid medicine to inflate the tube body like a balloon while moving only to the flow path of the fixed tube, or allow the liquid medicine to be injected while returning to the initial position due to pressure of the inflated balloon.

However, another packing mechanism may be required to maintain the airtightness while fixing the injection mechanism or stopper mechanism to the fixed tube, and another defect or various difficulties may be generated due to the assembly and fixation using the packing mechanism.

(Patent Document 1) KR10-1535947 B1
(Patent Document 2) KR10-1125478 B1
(Patent Document 3) KR10-1278492 B1

SUMMARY OF THE INVENTION

Accordingly, the present disclosure is provided to be miniaturized by removing a dead space, facilitate assembly, and eliminate defects after the assembly.

To this end, according to the present disclosure, when a tube body is provided outside a fixed pipe, both ends of the tube body may be folded and inserted into both ends of the fixed tube, so as to remove the dead space while being inserted inside the case.

In addition, in a state where the both ends of the tube body are folded and inserted into the both ends of the fixed tube, an injection mechanism for injecting the liquid medicine or a stopper mechanism may be coupled while pressing the tube body folded inward, so that a separate packing may be unnecessary and the airtightness may be maintained.

In addition, with regard to the injection mechanism and the stopper mechanism, one tightening mechanism may be connected and fixed to the injection mechanism by passing through the stopper mechanism from the outside of the case using, so that the injection mechanism and the stopper mechanism may be fixed and the case may be fixed at once.

In addition, in order to prevent an occurrence of a residual liquid medicine because a step is generated due to the thickness of the tube body when the tube body is folded and inserted into both ends of the fixed tube, stepped surfaces may be provided inside the both ends of the fixed tube.

In addition, when the injection mechanism and the stopper mechanism are inserted inside the fixed tube, the insertion tubes may be formed to have predetermined lengths longer than a length of the folded tube body such that the injection mechanism or the stopper mechanism may be pressed in close contact with the folded and inserted tube body, and the injected liquid medicine may be transferred to the tube body, and the injection mechanism may be formed with an inwardly elongated insertion groove and formed at a tip thereof with a flow path hole so as to communicate with the flow path hole formed in the fixed tube.

In addition, a tip of the insertion tube may be formed with a helical portion to be tightened with the tightening mechanism, so as to be engaged with and fixed to a helical portion of the tightening mechanism.

In addition, a recess groove may be formed on a circumference having a flow path hole of the insertion tube, so as to be easily communicate with the flow path of the fixed tube when the liquid medicine is injected or discharged.

In addition, the injection mechanism and the stopper mechanism provided at one end of the insertion tube may have outer diameters larger than an outer diameter of the tube body when coupled to the fixed pipe, so as to seal the both ends of the fixed tube.

In addition, the injection mechanism may be formed with a flange, so that the fixed tube is closely coupled to the case by the flange when coupled to the case.

Thus, according to the present disclosure, the tube body positioned outside of the fixed tube covers the entire outer diameter of the fixed tube, and the tip of the tube body is mounted to be folded into the fixed tube, so that unnecessary dead space can be prevented from being generated inside the case when the tube body is contracted or inflated while covering the entire outer diameter of the fixed tube when the liquid medicine is filled, thereby minimizing the volume and weight, so that the compact liquid medicine injector can be provided.

In addition, according to the present disclosure, the residue, which is caused by a protrusion formed inside the mounting hole, of the expensive liquid medicine can be minimized, and a connecting tube can be mounted or assembled even when a flow hole and a connection hole of the fixed tube do not match in communication with each other.

In addition, according to the present disclosure, even when a flow path and a compartment formed inside the connecting tube are defined to have sizes different from each other, an insertion frame formed on an outer side can prevent a deformation due to a cooling speed difference during injection molding.

BRIEF DESCRIPTION OF THE DRAWINGS

The above and other aspects, features, and advantages of certain embodiments of the disclosure will be more apparent from the following description taken in conjunction with the accompanying drawings, in which.

DETAILED DESCRIPTION OF THE INVENTION

First, the terms used in the specification and claims of the present disclosure should not be construed as limited to a lexical meaning, and should be construed as the meanings and concepts consistent with the technical idea of the present disclosure, based on the principle that "an inventor may define the concept of the term properly in order to describe the invention in the best way".

Accordingly, the embodiments described in the specification and the configurations shown in the drawings are merely preferred embodiments according to the present disclosure, and do not represent all of the technical ideas of the present disclosure. Therefore, it should be understood that various equivalents and modifications may be substituted therefor at the time of filing of the present application.

Hereinafter, the embodiments for carrying out the present disclosure will be described in detail with reference to the accompanying drawings.

Figure 2:
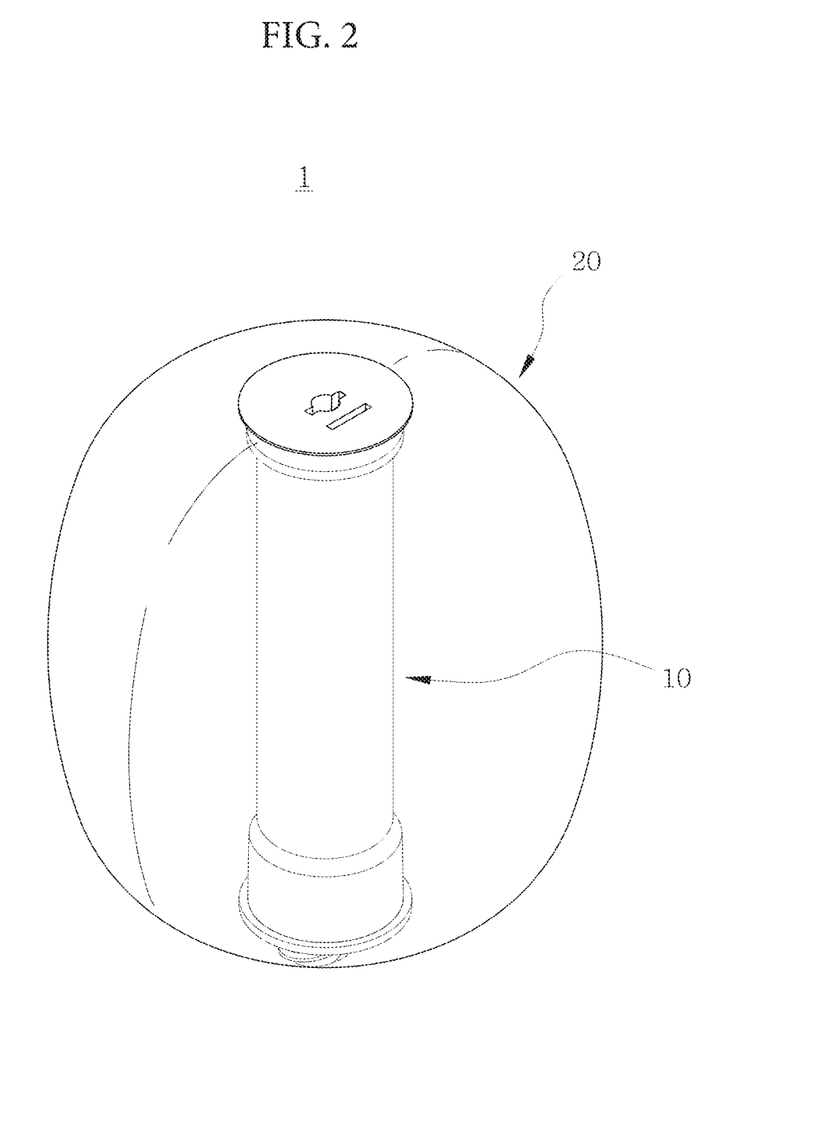
FIG. 2 is a perspective view showing an overall appearance of the present disclosure.
Figure 3:
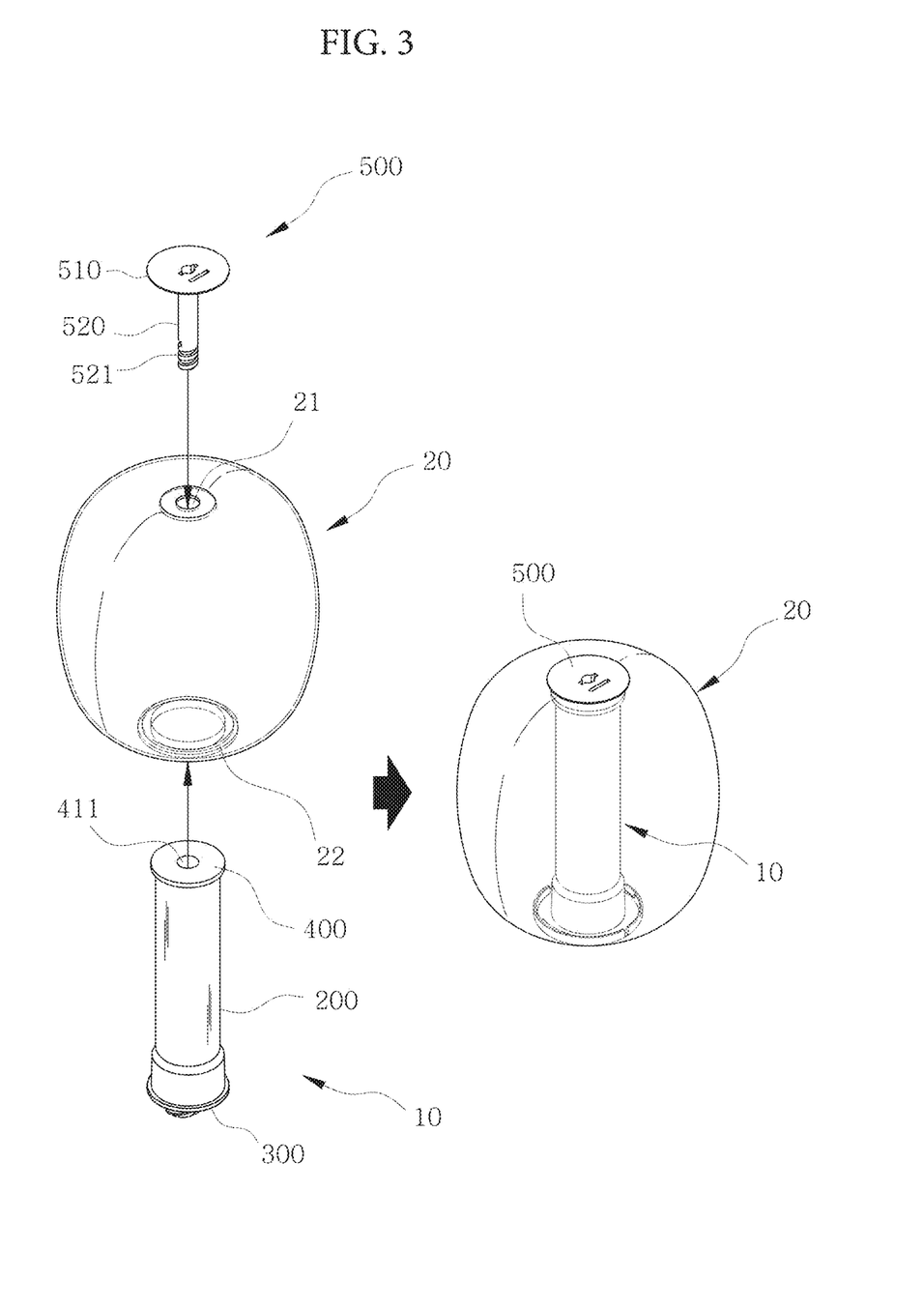
FIG. 3 is a view showing a tube body mounted to a fixed tube according to one embodiment of the present disclosure.
Figure 4:
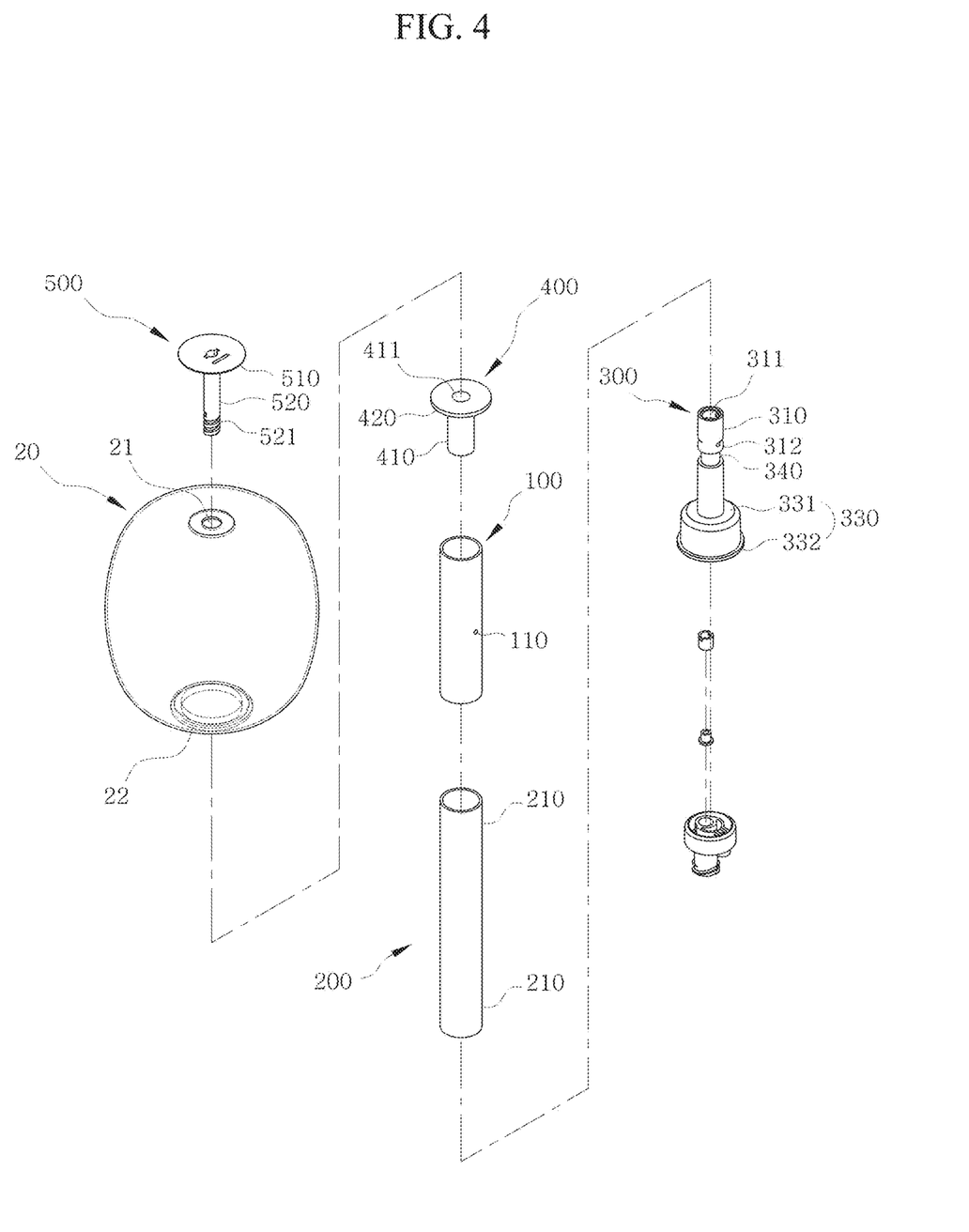
FIG. 4 is a view showing a tube body mounted to a fixed tube according to another embodiment of the present disclosure.

FIG. 2 shows that a tube body constituting a balloon portion is mounted to a fixed tube in a liquid medicine injector according to the embodiment of the present disclosure. FIG. 3 show that a protrusion formed inside of the fixed tube in which both ends of the tube body are folded. FIG. 4 shows an assembling process of the balloon and the liquid medicine injector.

Referring to the above drawings, a liquid medicine injector 1 according to the embodiments of the present disclosure includes a hollow fixed tube 100 having a flow path hole in an outer wall thereof; a balloon portion 10 in which a clogged structure is formed in by a stopper mechanism at one end of the fixed tube in a state in which a hollow tube body 200 surrounding and coupled in close contact with an outer side of the fixed tube is mounted in close contact with the fixed tube, an injection mechanisms capable of injecting the liquid medicine is mounted at the other end to maintain airtightness at the both ends of the fixed tube, the liquid medicine inflates the tube body through the flow path hole of the fixed tube when the liquid medicine is injected by the injection mechanism, and the inflated tube body is contracted and the liquid medicine is injected through the flow path hole to inject the injected liquid medicine; and a case 20 for accommodate the balloon portion 10 as a whole, wherein the fixed tube 100 constituting the balloon portion 10 and the case 20 surrounding the balloon portion 10 may be generally injected or blow-molded using plastic in view of economic or handling feasibilities or the like, and the tube body 200 may be formed of silicone, plastic, or rubber that are harmless to a human body.

As shown in FIG. 4, according to the present disclosure, the tube body 200 is provided relatively longer than the length of the fixed tube 100, and the tube body 200 in the above state is coupled to surround the fixed tube 100, so that both ends of the tube body 200 further extend from both ends of the fixed tube 100 to constitute exposure ends 210.

The exposure ends 210 are folded and inserted into the fixed tube 100, thereby coming into close contact with an inner wall 101 of the fixed tube.

Figure 5:
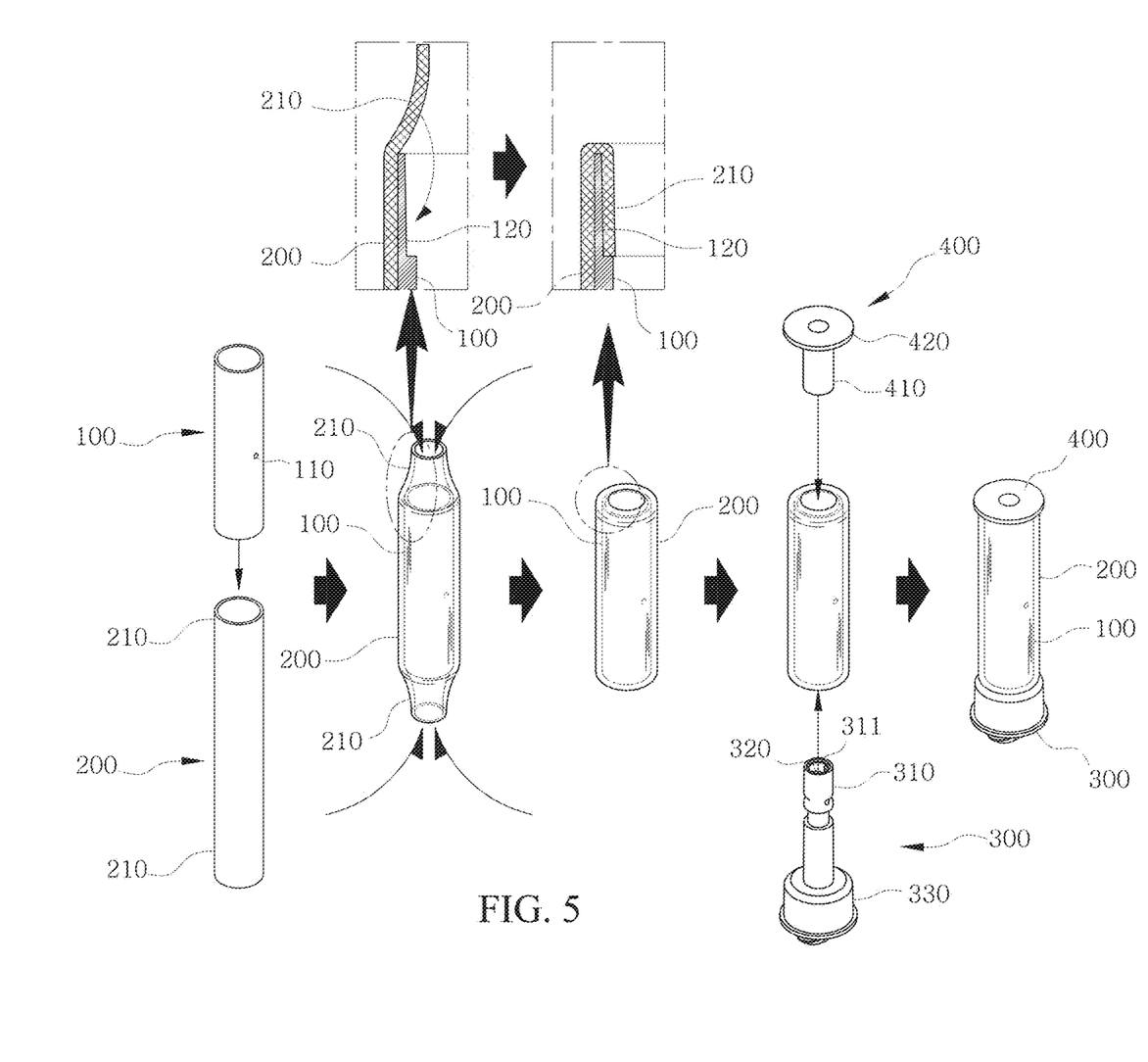
FIG. 5 is a view showing an exposed surface of the tube body fixed by an injection mechanism and a stopper mechanism while being folded according to one embodiment of the present disclosure.

In addition, in a state where the exposure ends 210 of the both ends of the tube body 200 are folded and inserted into the both ends of the fixed tube 100, the injection mechanism 300 for injecting the liquid medicine or the stopper mechanism 400 is coupled while pressing the exposure ends of the tube body folded inward and coming into close contact with the inner wall of the fixed tube, so that a separate packing is unnecessary at the both ends of the fixed tube, thereby maintaining the airtightness in a state where the injection mechanism 300 or the stopper mechanism 400 is coupled.

Accordingly, since the tube body starts to swell from tips at the both ends of the fixed tube when the tube body surrounding the fixed tube is inflated, a dead space may not exist while being inserted inside the case.

In addition, in a state where the injection mechanism and the stopper mechanism are coupled to the both ends of the fixed tube, one tightening mechanism 500 is used to prevent an arbitrary separation to fix the case 20 and connect and fix the injection mechanism 300 and the stopper mechanism 400.

To this end, the tightening mechanism 500 is composed of a flange 510 and a tightening shaft 520, a helical portion 521 is formed at a tip of the tightening shaft 520, and an insertion hole 21, to which the tightening shaft 520 is inserted, is formed at one end of the case 20. Thus, the tightening shaft 520 of the tightening mechanism 500 is inserted through the insertion hole 21 to pass through the stopper mechanism 400 so as to be connected and fixed to the injection mechanism 300, so that the injection mechanism and the stopper mechanism can be fixed and the case can be fixed at once.

When the injection mechanism 300 and the stopper mechanism 400 are coupled to the both ends of the fixed tube 100, insertion tubes 310 and 410 are formed to have a predetermined length longer than lengths of the exposure ends 210 of the folded tube body, such that the injection mechanism or the stopper mechanism may be pressed in close contact with the tube body folded and inserted into the both ends of the fixed tube and the injected liquid medicine may be transferred to the tube body, and the insertion tube 310 of the injection mechanism is formed therein with an inwardly elongated insertion groove 311 and formed at a tip thereof with a flow path hole 312 so as to communicate with the flow path hole 110 formed in the fixed tube 100.

It is an advantage that the flow path hole 110 of the fixed tube and the flow path hole 312 formed at the tip of the insertion groove of the insertion tube may be positioned on the same line, such that the injection and outflow of the liquid medicine can be facilitated.

Figure 6:
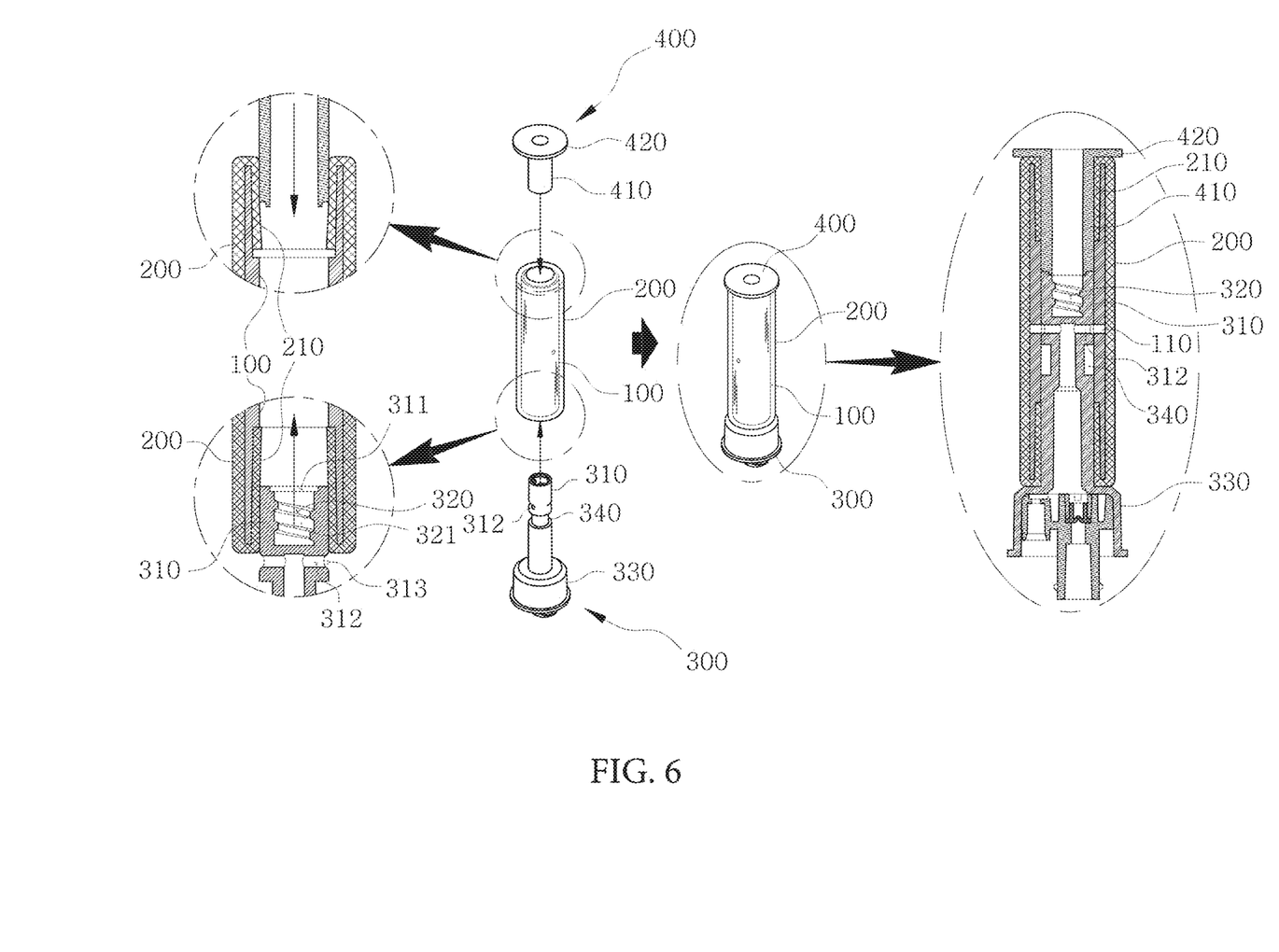
FIG. 6 is a view showing a state in which tips of the injection mechanism and the stopper mechanism of the present disclosure engaged with each other.

In addition, a tip of the insertion tube 310 is formed therein with a helical groove 320 having a helical portion 321 so as to be engaged and fixed with the helical portion 521 provided at the tip of the tightening shaft 520 of the tightening mechanism.

The stopper mechanism 400 is also formed with the insertion tube 410, the insertion tube 410 is also formed longer than the folded exposure end 210, and a through-hole 411 is formed inside the insertion tube 410, so that the tightening shaft 520 of the tightening mechanism is inserted into the helical groove 320 of the injection mechanism 300 while passing through the insertion tube 410, engaged with the helical portion 321, and connected and coupled to the stopper mechanism 400 and the injection mechanism 300, thereby being fixed to the fixed tube while maintaining the airtightness.

In addition, the injection mechanism and the stopper mechanism are provided with cover portions 330 and 420 capable of blocking the both ends of the fixed tube in a state in which the insertion tubes 310 and 410 having predetermined lengths are provided, respectively, and outer diameters of the cover portions 330 and 420 are formed to be larger than an outer diameter of the coupled tube body 200 while surrounding the fixed tube 100 so as to seal the both ends of the fixed tube 100 surrounded by the tube body.

In other words, when tightened and fixed by the tightening mechanism 500 as described above, pressing frames 331 and 421 of the cover portions 330 and 420 having larger diameters than the insertion tubes 310 and 410 pressurize exposed edges 211 of the exposure ends 210, respectively, while being folded and inserted into the both ends of the fixed tube and coming into close contact with the inner wall of the fixed tube, so that the airtightness between the fixed tube and the tube body may be maintained.

Figure 7:
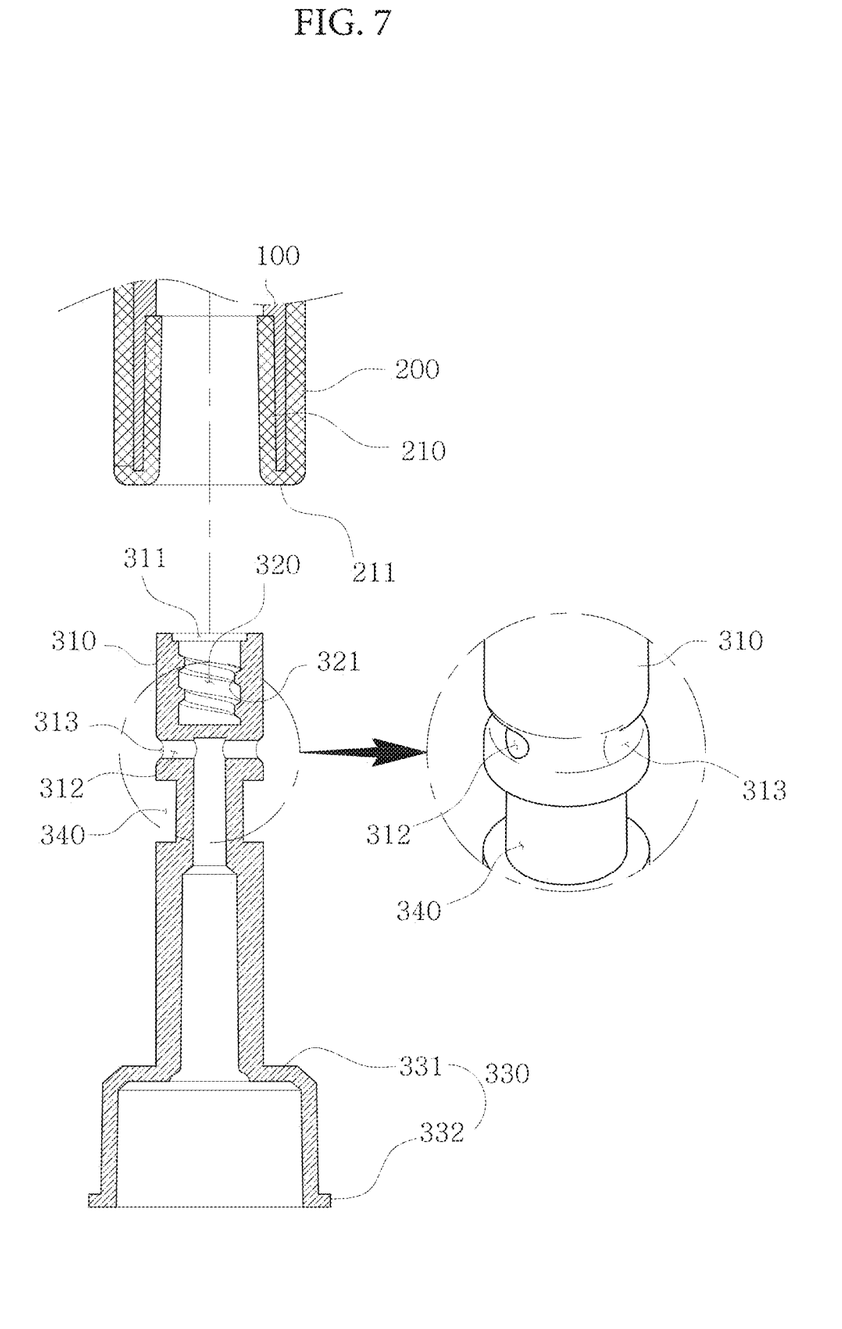
FIG. 7 is a view showing a recess groove formed in the injection mechanism according to one embodiment of the present disclosure.
Figure 10:
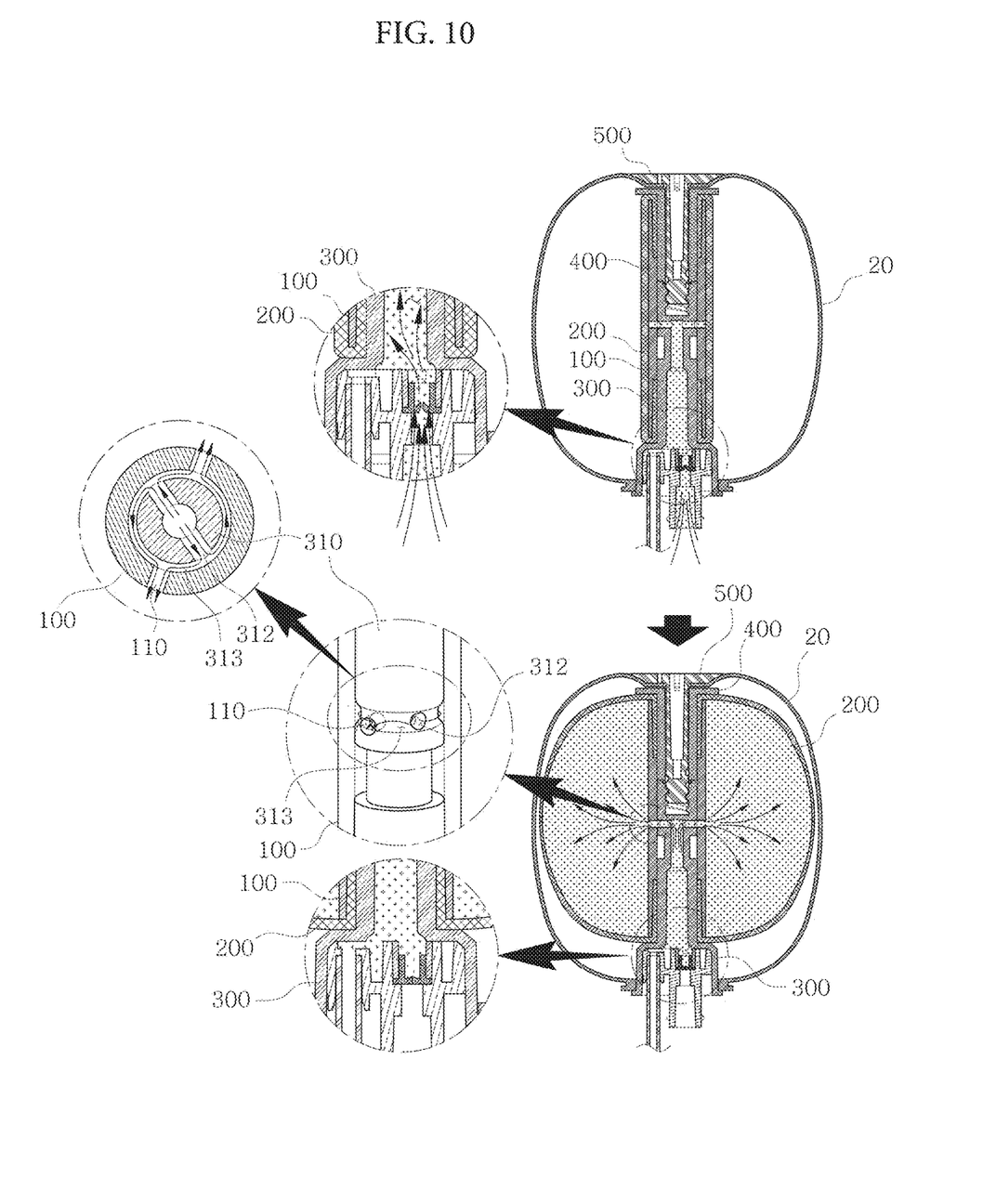
FIGS. 10 and 11 are views showing a state in which the injected liquid medicine flows through a flow path hole of the fixed tube due to a recess groove according to one embodiment.
Figure 11:
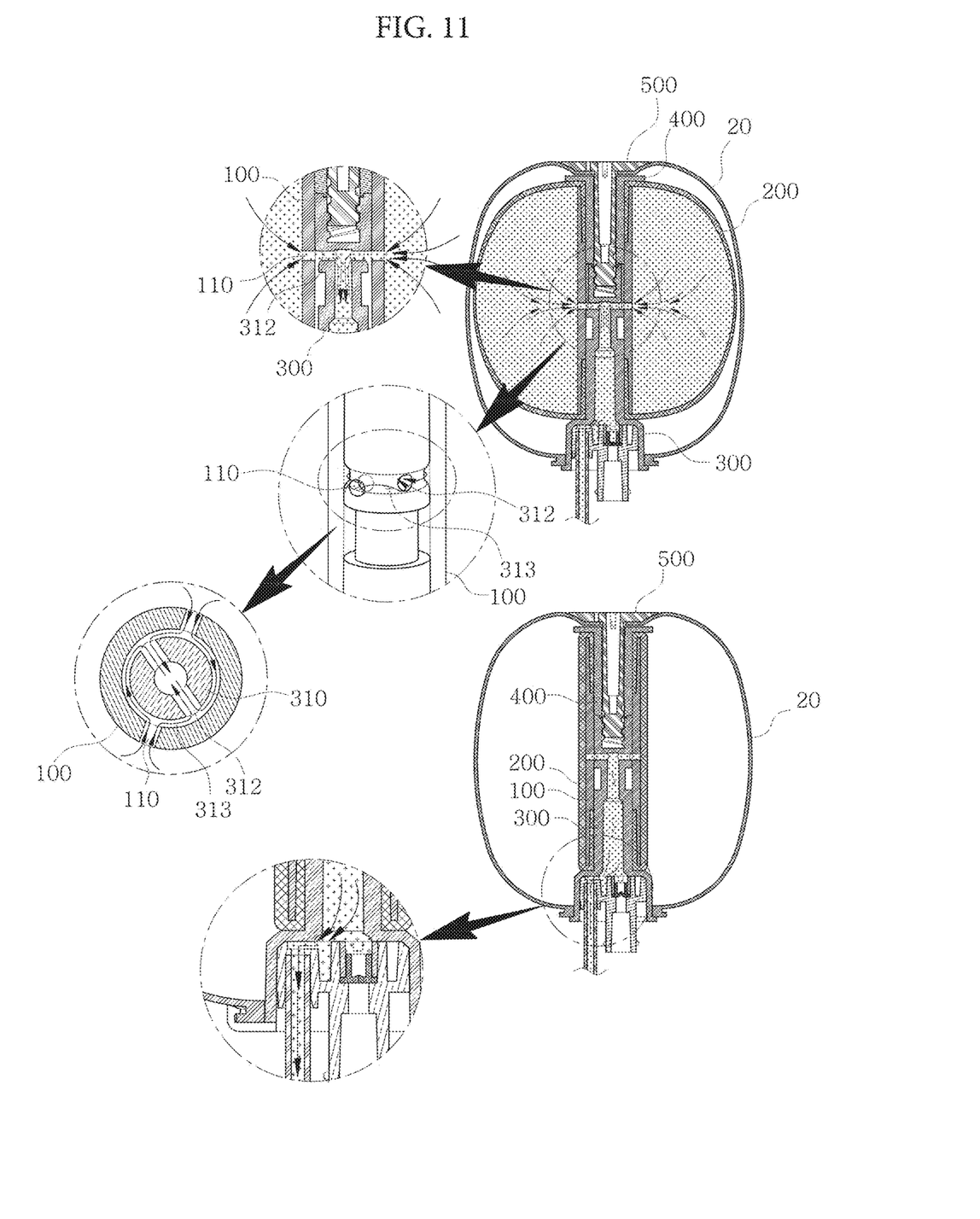
Figure 12:
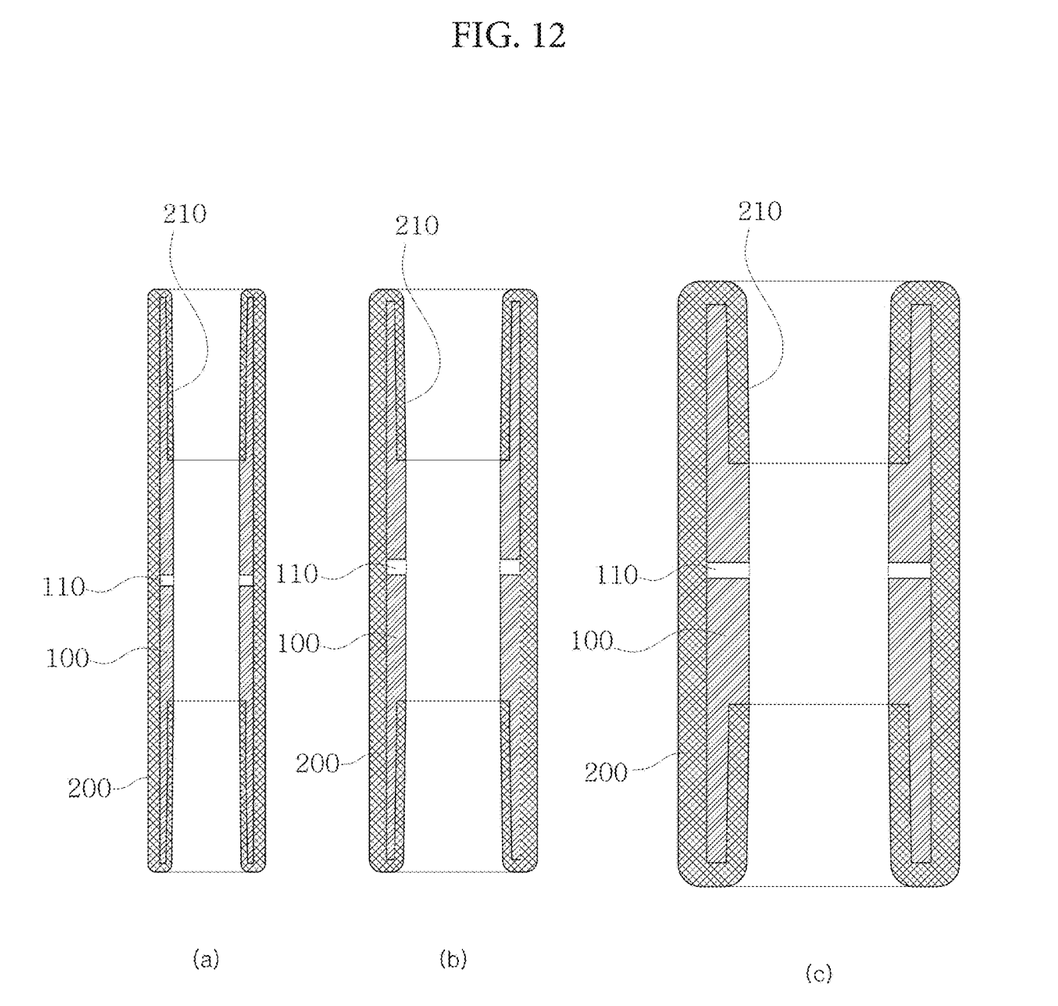
FIG. 12 is a sectional view showing various sizes of the fixed tube and the tube body according to one embodiment.

In addition, a recess groove 313 is formed on a circumference having the flow path hole 312 at the tip of the insertion tube 310, so that the liquid medicine may be easily discharged to the flow path 110 of the fixed tube 100 through the recess groove 313 in the case of injection or discharge of the liquid medicine, even when the flow path hole 312 of the insertion tube and the flow path hole 110 of the fixed tube are arranged not to communicate with each other, that is, even when arranged offset.

In addition, in order to prevent the case of generating a residual liquid medicine because a step protrudes from the inner wall of the fixed tube due to the thickness of the tube body when the exposure ends 210 of the tube body are folded inside the both ends of the fixed tube 100 and come into close contact with the inner wall of the fixed tube 100, stepped surfaces 120 are provided inside the both ends of the fixed tube 100, such that the exposure ends 210 of the tube body are placed on the exposed stepped surfaces 120 while being folded inward to form a horizontal level.

To this end, the depth of the stepped surface corresponds to the thickness of the exposure end.

Figure 8:
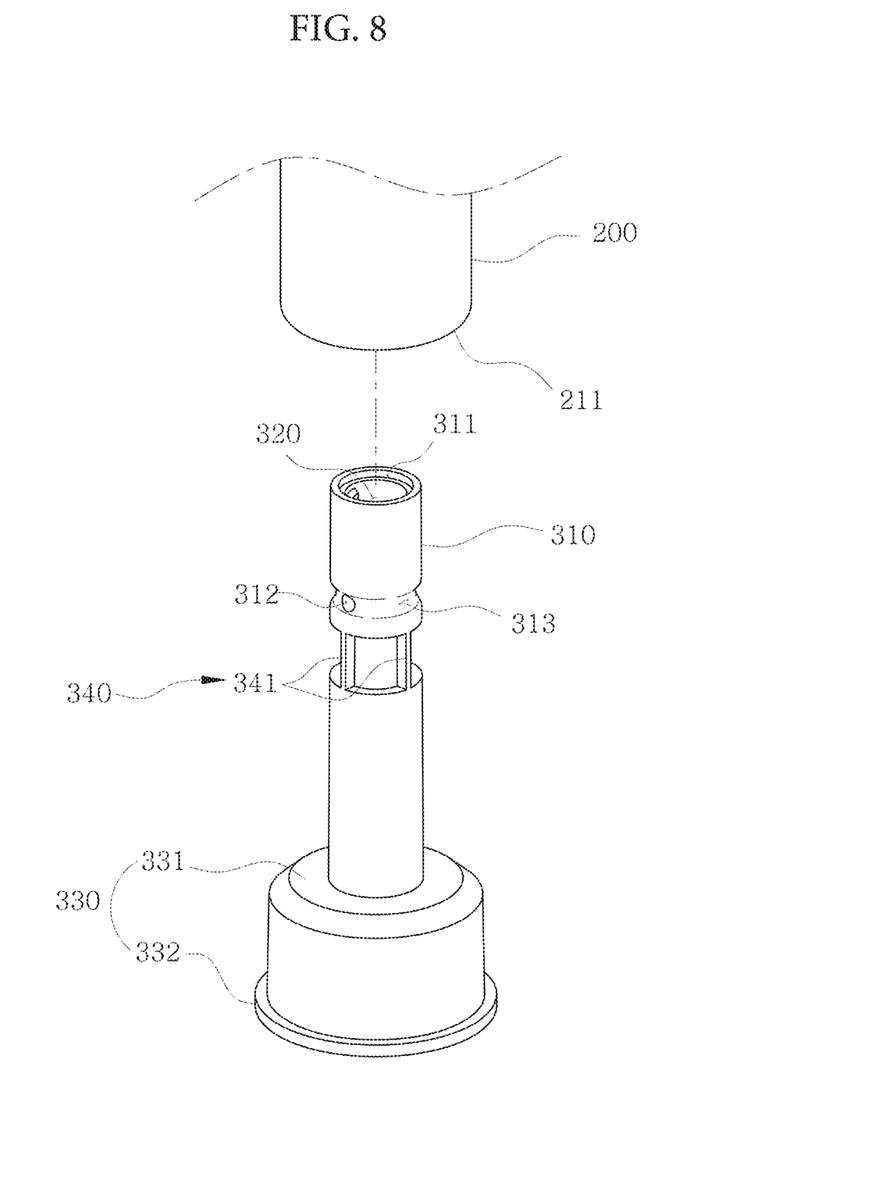
FIG. 8 is a view showing that ribs are provided on a cut-way groove according to one embodiment of the present disclosure.

In addition, in the state that the flow path hole is formed in the recess groove at the tip of the insertion tube, a cut-way groove 340 is formed at a rear side thereof to prevent the insertion tube from being deformed during injection molding, in which ribs 341 are formed at regular intervals to minimize the residue due to the cut-way groove 340.

Figure 9:
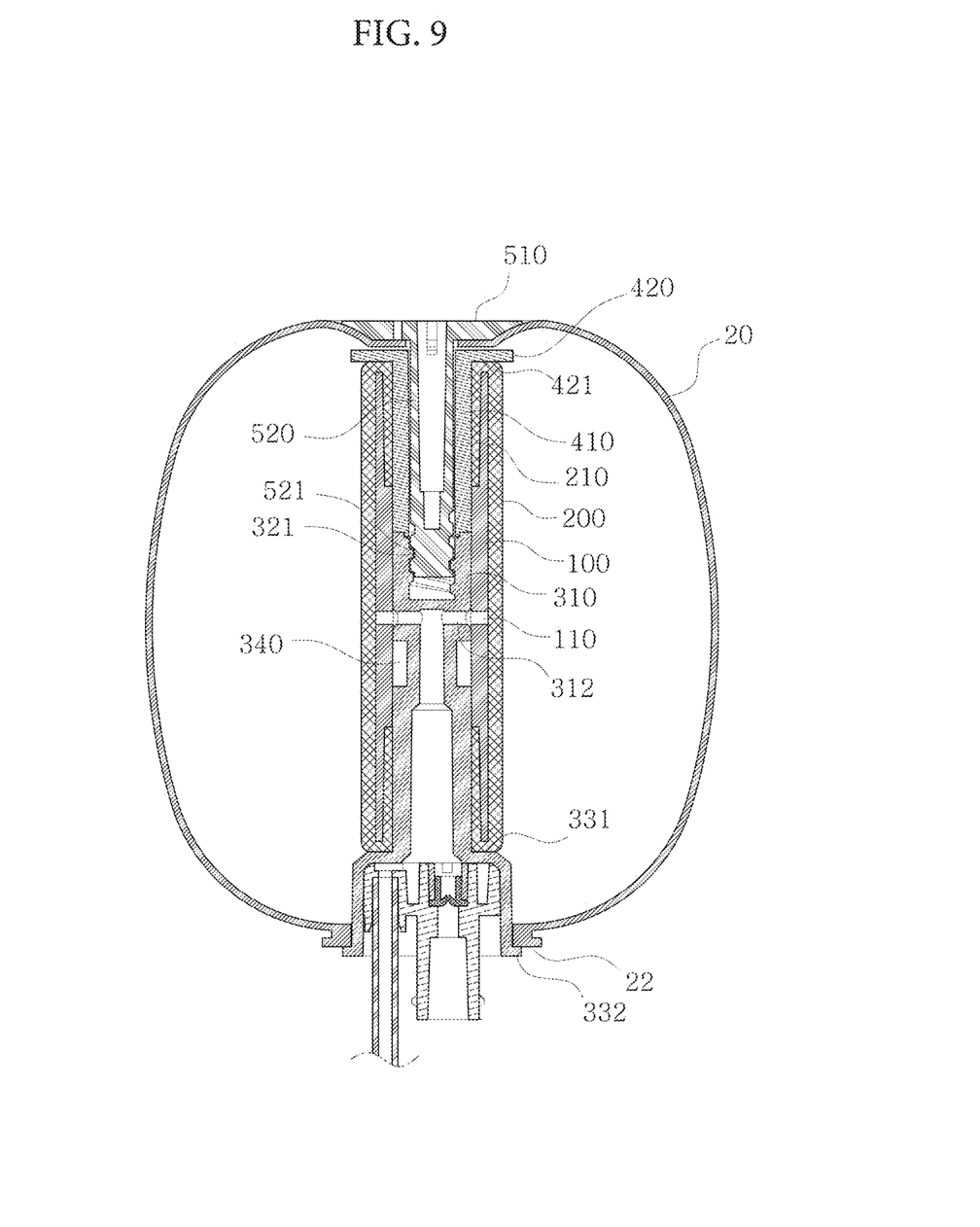
FIG. 9 is a sectional view of an assembled state of the present disclosure.
Figure 13:
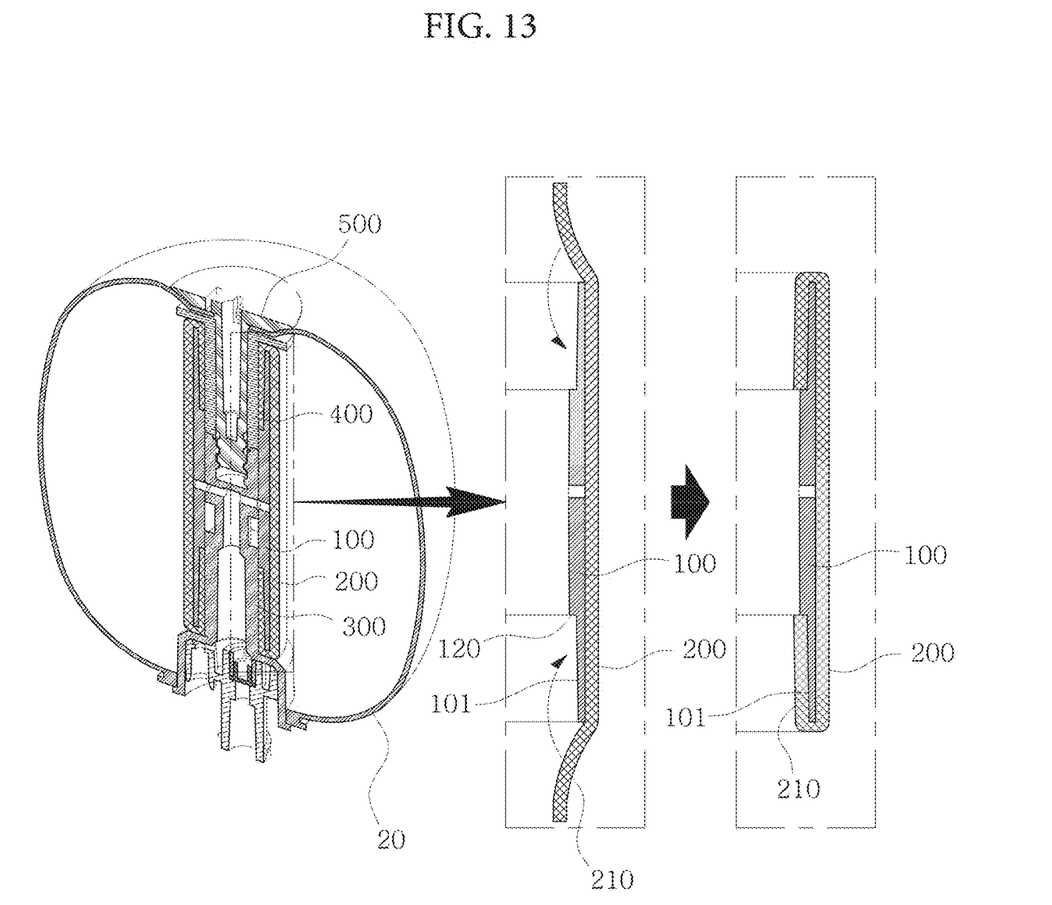
FIG. 13 is a sectional perspective view showing an assembled state of the present disclosure.
Figure 14:
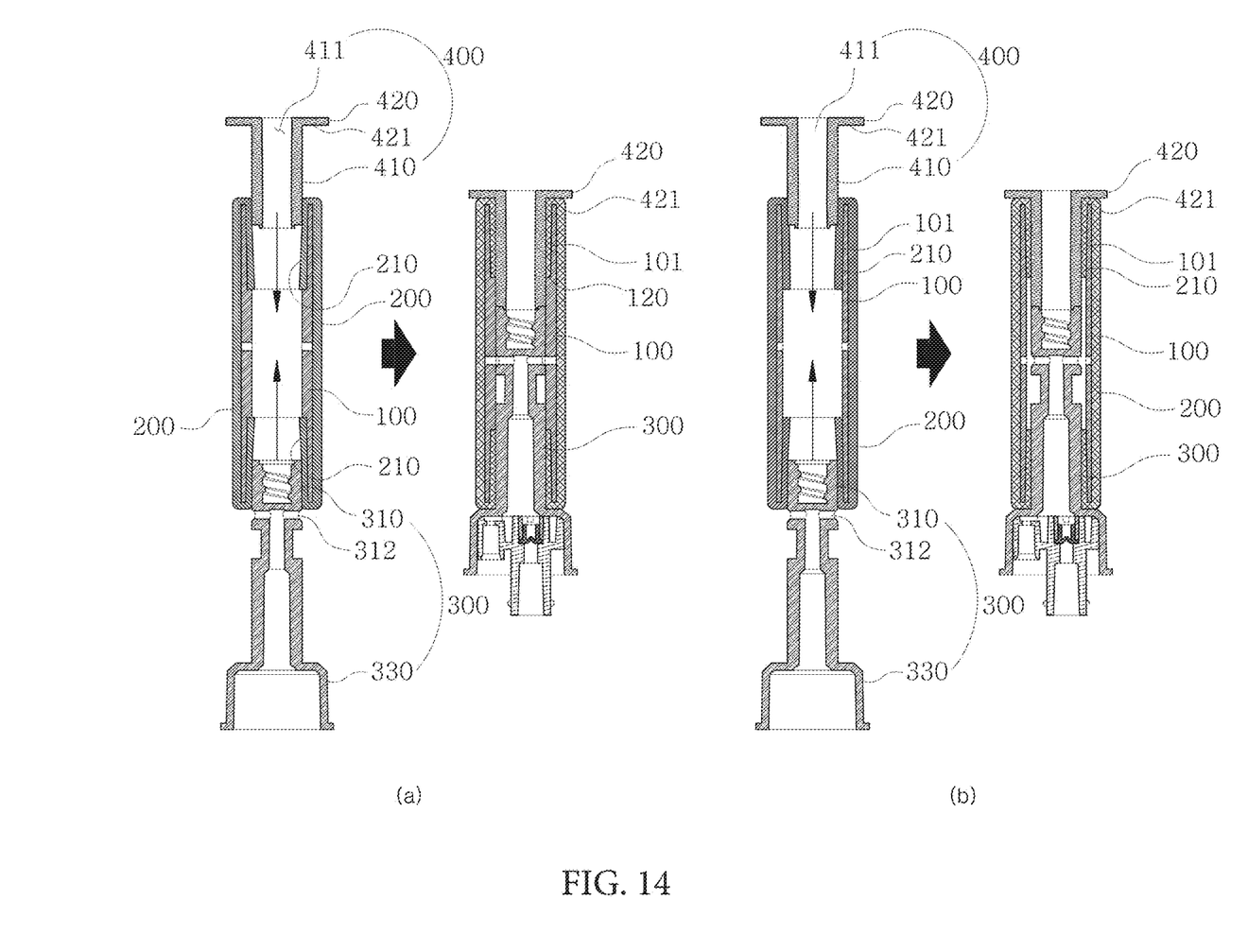
FIG. 14 is a sectional view showing the tube body assembled using an injection mechanism and a stopper mechanism while being assembled to the fixed tube according to one embodiment of the present disclosure.

In addition, when the balloon portion 10 is inserted and fixedly coupled to the case 20, a flange 332 extending outward is formed at the cover portion 330 of the injection mechanism of the fixed tube of the balloon portion 10, and one side of the case is provided with a mount frame 22 to allow the flange 332 to be seated thereon, the other side of the case is formed with the insertion hole 21 as described above, and a seating portion is formed to be mounted thereon with the flange of the tightening mechanism when the case is tightened by the tightening mechanism 500, thereby preventing a portion latched outward on the case while being coupled.

The present disclosure has been described with reference to the accompanying drawings, but the descriptions are merely exemplary illustrations and it will be understood by those skilled in the art that various changes and modifications may be made based on the doctrine of equivalents. Accordingly, the actual scope of the present disclosure will be defined by the appended claims and their equivalents.

What is claimed is:

1. A balloon type liquid medicine injector comprising:
a hollow fixed tube (100) having a flow path hole formed in an outer wall of the hollow fixed tube; and
a tube body (200) extending longer than a length of the fixed tube,
wherein both ends of the tube body (200) further extend from both ends of the fixed tube (100) to form exposure ends (210), respectively, in a state where the tube body (200) is coupled to surround the fixed tube (100) while being inflated, and
wherein the exposure ends (210) are folded and inserted into the fixed tube (100), thereby coming into close contact with an inner wall (101) of the fixed tube, so as to form a balloon member in which an injector mechanism and a stopper mechanism are mounted to the exposure ends.

2. The balloon type liquid medicine injector of claim 1, wherein, in a state where the exposure ends (210) of the both ends of the tube body (200) are adapted to be folded and inserted into the both ends of the fixed tube (100), the injector mechanism (300) for injecting the liquid medicine and the stopper mechanism (400) are adapted to be coupled while by pressing the exposure ends of the tube body folded inward so as to come into close contact with the inner wall of the fixed tube, so that a separate packing is unnecessary at the both ends of the fixed tube, thereby maintaining an airtightness in a state where the injector mechanism (300) or the stopper mechanism (400) is coupled.

3. The balloon type liquid medicine injector of claim 1, wherein, in a state where the injector mechanism and the stopper mechanism are adapted to be coupled to the both ends of the fixed tube, a tightening mechanism (500) having a flange (510) and a tightening shaft (520) is adapted so as to prevent an arbitrary separation to fix a case (20) and connect and fix the injector mechanism (300) and the stopper mechanism (400).

4. The balloon type liquid medicine injector of claim 3, wherein the tightening mechanism (500) having the flange (510) and the tightening shaft (520) includes:
a helical portion (521) is formed at a tip of the tightening shaft (520), and
an insertion hole (21), to which the tightening shaft (520) is inserted, is formed at one end of the case (20), and
wherein the tightening shaft (520) of the tightening mechanism (500) is adapted to be inserted through the insertion hole (21) to pass through the stopper mechanism (400) so as to be connected and fixed to the injector mechanism (300), so that the injector mechanism and the stopper mechanism are fixed and the case is fixed at once.

5. The balloon type liquid medicine injector of claim 4, wherein, when the injector mechanism (300) and the stopper mechanism (400) are coupled to the both ends of the fixed tube (100), insertion tubes (310) and (410) are formed to have a predetermined length longer than lengths of the folded exposure ends (210) of the tube body, such that the injector mechanism or the stopper mechanism may be pressed in close contact with the tube body folded and inserted into the both ends of the fixed tube and an injected liquid medicine is easily transferred to the tube body, and the insertion tube (310) of the injector mechanism is formed therein with an inwardly elongated insertion groove (311) and formed at a tip thereof with a flow path hole (312) so as to communicate with the flow path hole (110) formed in the fixed tube (100).

6. The balloon type liquid medicine injector of claim 5, wherein the flow path hole (110) of the fixed tube and the flow path hole (312) formed at the tip of the insertion groove of the insertion tube are positioned on a same line, a recess groove (313) is formed on a circumference having the flow path hole (312) at the tip of the insertion tube (310), so that the liquid medicine is easily discharged to the flow path (110) of the fixed tube (100) through the recess groove (313) when the liquid medicine is injected or discharged even when the flow path hole (312) of the insertion tube and the flow path hole (110) of the fixed tube are arranged not to communicate with each other.

7. The balloon type liquid medicine injector of claim 6, wherein the tip of the insertion tube (310) having a helical groove (320) in the tip of the insertion tube (310) to be engaged and fixed with a helical portion (521) provided at the tip of the tightening shaft (520) of the tightening mechanism.

8. The balloon type liquid medicine injector of claim 5, wherein the insertion tube (410) is provided with the stopper mechanism (400), and
wherein the insertion tube (410) is formed longer than each of the folded exposure ends (210), and a through-hole (411) is formed inside the insertion tube (410), so that the tightening shaft (520) of the tightening mechanism is adapted to be inserted into a helical groove (320) of the injector mechanism (300) while passing therethrough, engaged with the helical portion (321), and connected and coupled to the stopper mechanism (400) and the injector mechanism (300), thereby being fixed to the fixed tube to maintain an airtightness.

9. The balloon type liquid medicine injector of claim 8, wherein the injector mechanism and the stopper mechanism are provided with cover portions (330 and 420) capable of blocking the both ends of the fixed tube in a state in which the insertion tubes (310 and 410) having predetermined lengths are provided, respectively, and outer diameters of the cover portions (330 and 420) are formed to be larger than an outer diameter of the coupled tube body (200) while surrounding the fixed tube (100) so as to seal the both ends of the fixed tube (100) surrounded by the tube body.

10. The balloon type liquid medicine injector of claim 1, wherein, in order to prevent an occurrence of generating a residual liquid medicine because a step protrudes from the inner wall of the fixed tube due to a thickness of the tube body when the exposure ends (210) of the tube body are folded inside the both ends of the fixed tube (100) and come into close contact with the inner wall of the fixed tube (100), stepped surfaces (120) are provided inside the both ends of the fixed tube (100), such that the exposure ends (210) of the tube body are placed on the exposed stepped surfaces (120) while being folded inward to form a horizontal level.

11. The balloon type liquid medicine injector of claim 6, wherein, in the state that the flow path hole is formed in the recess groove at the tip of the insertion tube, a cut-way groove (340) is formed at a rear side of the tip of the insertion tube so as to prevent the insertion tube from being deformed during injection molding.

12. The balloon type liquid medicine injector of claim 11, wherein ribs (341) are formed at regular intervals to minimize a residue of a liquid medicine due to the cut-way groove (340).

13. The balloon type liquid medicine injector of claim 3, wherein, when a balloon portion (10) is inserted and fixedly coupled to the case (20), a flange (332) extending outward from a cover portion (330) of the injector mechanism of the fixed tube of the balloon portion (10), and one side of the case is provided with a mount frame (22) to allow the flange (332) to be mounted thereon, and a seating portion is formed to be mounted thereon with the flange of the tightening mechanism when the case is tightened by the tightening mechanism (500) in a state in which the other side of the case is formed with an insertion hole (21), thereby preventing a portion latched outward on the case while being coupled.

* * * * *